US00PP27475P2

(12) United States Plant Patent
Kubby

(10) Patent No.: US PP27,475 P2
(45) Date of Patent: Dec. 20, 2016

(54) ***CANNABIS* PLANT NAMED 'ECUADORIAN SATIVA'**

(50) Latin Name: ***Cannabis sativa;* ssp. *sativa* and *Cannabis sativa* ssp. *indica* (Lam.)**
Varietal Denomination: Ecuadorian Sativa

(75) Inventor: Steven Wynn Kubby, South Lake Tahoe, CA (US)

(73) Assignee: KUBBY PATENT AND LICENSES, LIMITED LIABILITY COMPANY, Burnet, TX (US)

( * ) Notice: Subject to any disclaimer, the term of this patent is extended or adjusted under 35 U.S.C. 154(b) by 779 days.

(21) Appl. No.: 12/661,271

(22) Filed: Mar. 13, 2010

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

PUBLICATIONS

Forapani et al. Comparison of Hemp Varieties Using Random Amplified Polymorphic DNA Markers. Crop Science 41:1682-1689 (2001).*

Recommended Methods for the Identification and Analysis of *Cannabis* and *Cannabis* Products.http://www.unodc.org/documents/scientific/ST-NAR-40-Ebook.pdf 2009.*

* cited by examiner

*Primary Examiner* — Annette Para

(74) *Attorney, Agent, or Firm* — Jacobson Holman, PLLC.

(57) ABSTRACT

Unique herbaceous annual '*Cannabis sativa*' female plants, having numerous glandular flowers in a congested and elongated inflorescence, hollow stems a characteristic of the fiber-producing strains of '*Cannabis sativa* ssp. *sativa*' but absent in strains of '*Cannabis sativa* ssp. *indica*.' The plants are intoxicating, characteristic of '*Cannabis sativa*, ssp. *indica*', but absent in subspecies *sativa*. The new strain has energizing and motivating psychoactive effects as opposed to the lethargy normally associated with ssp. *indica* and show hypotensive effects. Morphologically, the plants have a few branched hairs on the stem that are not characteristic of the species, but are ordinary in most other respects.

3 Drawing Sheets

The *Cannabis* plant named '*Ecuadorian Sativa*' having a laboratory name of 'CTS-A' a variety of a cross between '*Cannabis sativa*; ssp. *Sativa*' and '*Cannabis sativa* ssp. *Indica* (Lam.)'.

BACKGROUND OF THE INVENTION

This invention relates to a novel hybrid of a cross between individuals thought to be of the two subspecies of '*Cannabis sativa* L.', '*Cannabis sativa*; ssp. *sativa*' and '*Cannabis sativa* ssp. *Indica*'.

HISTORICAL NOTE

Human cultivation history of *Cannabis* dates back 8000 years. Schultes, R E. 1970. Random thoughts and queries on the botany of *Cannabis*. Pages 11-38 in: CRB Joyce, and SH Curry eds., THE BOTANY AND CHEMISTRY OF *CANNABIS*. J. & A. Churchill. London, England. Hemp cloth recovered in Europe dates back 6000 years. (Small, E, Beckstead, H D, and Chan, A, 29(3) ECONOMIC BOTANY 29(3): 219-232 (1975). The written record of the pharmacologic properties of *Cannabis* goes back more than 4000 years. Ti, H. 2737 BC. NEI JING SU WEN HUANG TI (Yellow Emperor's Classic on Internal Medicine; referred to without citation in Small et al. 1975 Supra).

The taxonomy and nomenclature of the highly variable genus *Cannabis* (Emboden, W A, 29(3) ECONOMIC BOTANY 304-310 (1974)); (Small, E and Cronquist, A, 25(4) TAXON 405-435 (1976)); Small E and Cronquist, A 26(1) TAXON 110 (1977)); (Hillig, K W and Mahlberg, P G, 91(6) American Journal of Botany 966-975 (2004)), remains in question. This is in spite of the fact that its formal scientific name, '*Cannabis sativa* L.', assigned by Carolus Linneaus (Linnaeus, C, 2 SPECIES PLANTARUM 1027 (1753), Salvius, Stockholm. Facsimile edition, 1957-1959. Ray Society, London, U.K.), is one of the oldest established names in botanical history and is still accepted to this day. Another species in the genus, '*Cannabis indica* Lam.' was formally named somewhat later (de Lamarck, J B, 1(2) ENCYCLOPEDIE METHODIQUE DE BOTANIQUE, 694-5,(1785)), but is still very old in botanical history.

Three other species names were proposed in the 1800s to distinguish plants with presumably different characteristics (*C. macrosperma* Stokes, *C. chinensis* Delile, *C gigantean* Vilmorin), none of which are accepted today, although the epithet "indica" lives on as a subspecies of *C. sativa* ('*C. sativa* ssp. *indica* Lam.'. Small and Cronquist 1976 Supra).

In the 20th century, two new names were added to the liturgy of proposed '*Cannabis* species: *C. ruderalis*' Janischevsky and a hybrid, ×'*C. intersita*' Sojak. Small, E, Jui, P Y, and Lefkovitch, L P, 1(1) SYSTEMATIC BOTANY 1(1): 67-84 (1976); Small and Cronquist 1976, Supra. Further, numerous names have been proposed for horticultural variants of '*Cannabis*' but as of 1976, "very few of these have been validly published as formal taxa under the International Code of Botanical Nomenclature." Small and Cronquist 1976 Supra. Moreover, other recent work continues to focus on higher-order evolutionary relationships of the genus. *Cannabis* has been variously ascribed as belonging to the mulberry family (Moraceae) (Engler, H G A, Ulmaceae, Moraceae and Urticaceae, pages 59-118 (1889) in: A. Engler and K. Prantl eds., DIE NATURLICHEN PFLANZENFAMILIEN 3(1). W. Engelmann, Leipzig, Germany; Judd, W S, Sanders, R W, and Donoghue, M J, 5 HARVARD PAPERS IN BOTANY 5: 1-51 (1994)); nettle family (Urticaceae) (Berg, CC, Systematics and phylogeny of the Urticales, pages 193-220, in: P.R. Crane and S. Blackmore eds., EVOLUTION, SYSTEMATIC, AND FOSSIL HISTORY OF THE HAMAMELIDAE, VOL. 2, HIGHER HAMAMELIDAE, Clarendon Press, Oxford, U.K. (1989); Humpries, C J and Blackmore, S, A review of the classification of the Morcaceae, pages 267-277 In: Crane and Blackmore 1989 id.); and most recently in its own family with hops (Humulus), the Cannabaceae, or hemp family. Sytsma, K J, et al, 89(9) AMERICAN JOURNAL OF BOTANY 1531-1546 (2002).). While the work of Small and Cronquist 1976 Supra, seemed to effectively confine the genus to a single species with 2 subspecies (*C. sativa* s., *C.* s. *indica*), each with two varieties (*C. s.* s. var. *sativa, C. s.* s. var. *spontanea; C. s.* i. var. *indica, C. s.* i. var. *Kafiristanica*) largely on the basis of chemotaxonomy and interfertility of all forms, more recent work (Systma et al. 2002, Supra), proposes a two-species concept, resurrecting the binomial *C. indica* Lam. Since Sytsma et al. 2002 provides no key for discriminating between the species, the dichotomous key of Small and Cronquist 1976 Supra, which accounts for all forms in nature, whether wild or domesticated, was used to classify the characteristics of the plants described herein.

BRIEF SUMMARY OF THE INVENTION

The objective of the breeding program which produced the novel plant of this invention was primarily to develop a plant having the following characteristics: (a) medicinal properties that included hypotensive activity; (b) psychoactive properties that motivated and energized, rather than creating lethargy, sleepiness, and increased food consumption.

The biologically active chemicals found in plants, phytochemicals, affect the normal structure or function of the human body and in some cases treat disease. The mechanisms for the medicinal and psychoactive properties of a cannabis plant, like any medicinal herb, are the pharmacologic effects of its phytochemicals and for a medical cannabis plant, the key phytochemicals are cannabinoids and terpenes. Tetrahydrocannabinol, THC, is the primary psychoactive and medicinal cannabinoid and is the result of the decarboxylation of tetrahydrocannabinolic acid (THC-A), its acidic precursor. THC-A, (6ar,10ar)-1-hydroxy-6,6,9-trimethyl-3-pentyl-6a,7,8,10a-tetrahydro-6h-benzo-chromene-2-carboxylic acid, is found in the trichomes of the plant and converted into THC, which actually exists in only minute quantities in the living plant, after harvest and drying. Cannabigerol (CBG), Resorcinol, 2-(3,7-dimethyl-2,6-octadienyl)-5-pentyl-, is not considered psychoactive, is known to block the psychoactive effects of THC. and is considered medically active in a variety of conditions. Its precursor, cannabigerolic acid, CBG-A, (E)-3-(3,7-Dimethyl-2,6-octadienyl)-2,4-dihydroxy-6-pentylbenzoic acid, is being studied medically. Cannabichromene, CBC, and cannabidiol, CBD, are both non-psychoactive and end products of CBG metaolism, like THC, that are used medically Cannabichromenic acid; CBC-A, 5-hydroxy-2-methyl-2-(4-methylpent-3-enyl)-7-pentyl-chromene-6-carboxylic acid, is acidic cannabichromene.

'*Equadorian Sativa*' has been shown by laboratory testing by Steephill Labs to contain cannabinoid CBG-A at 2.49 mg/g, tetrahydrocannibidiol THC-A at 139.46 mg/g, THC at 2.24 mg/g and cannabinoid CBC-A at 1.75 mg/g. '*Equadorian Sativa*' cannabinoid content is dominated by its high content of THC (2.24 mg/g) and THC-A (139.46 mg/g).

Most varieties of high potency cannabis contain large quantities of three specific terpenes as well as various assortments of others. Those three terpenes are Beta-Myrcene, Beta Caryophyllene and Linalool. For instance, the variety CT3 has a profile with a high level of Beta-Myrcene, a moderate amount of Beta Caryophyllene and a small amount of Linalool, and a moderate amount of Limonene. '*Equadorian Sativa*' has an unusual complement of terpenes. There are small levels of Beta Myrcene, Beta Caryophyllene and Linalool, but the Limonene level is extraordinarily high at a level of 4.53, 10 to 20 times the usual range. This sets '*Equadorian Sativa*' apart from other varieties in its odor, the effects on mood and mentation and its medical qualities.

Physically, there are indications that its use may prevent some cancers and may cause apoptosis of cancer cells in vivo. There is a good possibility that the high levels of limonene may slow down the build-up of plaque in the arteries and reduce the effect of low-density lipo-proteins on the circulatory system. Indications are that '*Equadorian Sativa*' has many medical qualities that make it an important tool to maintain health and deal with illness.

The inventor cultivated various strains of '*Cannabis sativa*' in an effort to create a strain best suited to control his own disorder. This plant was derived from a female said to be of a strain called colloquially, 'Celestial Temple Sativa' an individual grown in Ecuador that reached a height of 23 ft (7 m), and was of the typical subspecies, '*Cannabis sativa* ssp. *sativa*'. The male parent is said to have been of a strain known colloquially as 'island sweet skunk' and reportedly to belonged to the subspecies '*Cannabis sativa* ssp. *indica* (Lam.)'. Small and Cronquist 1976 Supra. Neither 'Celestial Temple Sativa' nor 'island sweet skunk' has been patented in the United States or elsewhere, nor are they the subject of any pending patent applications of which the inventor is aware.

The particular plant disclosed herein was discovered in the area where the inventor was intentionally cross-pollinating and cultivating plants of cross between 'Celestial Temple Sativa' and 'island sweet skunk' described above using standard Mendelian breeding procedures well known to those of ordinary skill in the art. This resulted in the F1 generation of the inventor's cross, named 'Pleadian'. It was in the proximity of plants of the 'Pleadian' variety that had become hermaphroditic, in the inventor's garden in Lake Tahoe Calif. that he discovered one female plant that could only be reproduced assexually, by taking cuttings and that plant is the origin of this remarkable new strain. The female plant was discovered in a section of the inventor's hydroponic garden. The plant has been and continues to be assexually reproduced by cutting at the inventor's garden in Lake Tahoe Calif.

Comparison of the Steephill Laboratory terpenoid/cannabinoid profiles of '*Equadorian sativa*' with other plants with the same parents, 'island sweet skunk' and 'Celestial Temple Sativa' reveals that this plant, '*Equadorian sativa*' has a phenotypically unique profile, particular insofar as its levels of limonene. Two plants with the same parents were known by the laboratory names of CTK and CT3 and '*Equadorian sativa*' was tested by the laboratory name of CTA. Limonene found in '*Equadorian sativa*', were 45.35 mg/g while CTK and CT3 were only 2.24 mg/g and 1.03 mg/g respectfully. '*Equadorian sativa*' was shown to have substantially lower levels of cannabigerolic acid (CBG-A). cannabigerol (CBG) and Beta-Myrcene. '*Equadorian sativa*' had levels of only 2.49 mg/g of CBG-A while CTK had 6.1 mg/g CBG-A and CT3 had 8.13 mg/g of CBG-A. '*Equadorian sativa*' had only 0.001 mg/g of CBG while CTK had 0.3 mg/g CBG and CT3 had 0.54 mg/g of CBG. '*Equadorian sativa*' had only 1.1 mg/g Beta-Myrcene while CTK had 12.01 mg/g Beta-Myrcene and CT3 had 11.44 mg/g Beta-Myrcene.

This data is presented in tabular form in Table 1.

TABLE 1

| | Plant | | |
|---|---|---|---|
| Terpinoid or Cannabinoid | CTA mg/g | CTK mg/g | CT3 mg/g |
| CBG-A | 2.49 | 6.1 | 8.31 |
| CBG | 0.001 | 0.3 | 0.54 |
| Beta Myrcene | 1.1 | 12.02 | 11.44 |
| Limonene | 45.35 | 2.24 | 1.03 |

Asexual reproduction, colloqually known as "cloning" is a process well known to those of ordinary skill in the art of gardening and includes the following steps:

Step 1: From the female plant whose genetic profile is sought to be exactly reproduced, a 1"- 2" cutting is taken;

Step 2: The cutting of the desired plant and is placed in a rooting solution that may be water, or a B1 vitamin that is generally the content of a rooting or cloning powder or gel;

Step 3: The cutting and rooting solution are placed into a rooting medium such as rock wool and RAPID ROOTER® a peat moss product available at hydroponics stores, gardening supply stores, and from many Internet merchants and must be water retaining so that the roots can take water up into the leaves;

Step 4: The cutting in rooting solution and rooting medium is placed under a humidity dome that may be an inverted plastic cup or is available in kits 1'-2' long with a clear plastic dome to keep the humidity as high as possible to avoid the leaves drying before the cutting roots to insure viability;

Step 5: A a fluorescent light is placed just over the humidity dome that may be a generic work light available at hardware stores;

Step 6: One to two times a day, the humidity dome is removed for 30 seconds to insure the exchange of depleted air with fresh air to replenish the CO2.

Step 7: After maintaining this cutting in this manner, keeping the rooting medium wet at all times, for 5-14 days until root formation Step 8: The rooted plants are maintained under flourescent high intensity lights in a soil-less medium, with standard hydroponic fertilizers, for 14 weeks;

The plant observed and identified in the photographs was cultivated in this manner at a temperature between 76 and 80 degrees Fahrenheit and was 14 weeks of age. The new plant differs from its parents and related cultivars in that it has energizing and motivating psychoactive effects as opposed to the lethargy normally associated with ssp. indica and the instant plant also shows hypotensive effects.

Observation of the all female progeny of the original plant has demonstrated that this new and distinct variety has fulfilled the objectives and that its distinctive characteristics are firmly fixed and hold true from generation to generation vegetatively propagated from the original plant.

BRIEF DESCRIPTION OF THE PHOTOGRAPHS

The accompanying photographs illustrate the overall appearance of the new '*Equadorian sativa*' plants. These photographs show the colors as true as it is reasonably possible to obtain in reproductions of this type. Colors in the photographs may differ slightly from the color values cited in the detailed botanical description which accurately describe the colors of the new plant.

Sheet 1 'Cannabis CTS-A' shows the flower of the '*Equadorian sativa*' plant in the midst of leaves from above.

The photograph at the bottom of the Sheet 2, 'Cannabis CTS-A' comprises a close-up view of the flowering plant of '*Equadorian sativa*';

Sheet 3, 'Cannabis CTS-A' comprises a slightly oblique and very close view of the '*Equadorian sativa*'.

DETAILED BOTANICAL DESCRIPTION

The following is a detailed description of the new cultivar of '*Equadorian sativa*'.

The plant:

*Type* (*life form and habit*).—Herbaceous tap-rooted annual.

*Classification*.—Cultivars of '*Cannabis sativa*', possessing traits of the subspecies, '*C. sativa* ssp.. *indica* (Lam.)' When navigating the key of Small and Cronquist, Id., the first couplet separates individuals based on their ability to intoxicate. This cultivated line possesses intoxicating properties, and so the subspecies sativa and its varieties (var. sativa and spontanea) are eliminated from consideration. Within the next couplet distinguishing within the subspecies indica, fruits are required to separate between the varieties (var. indica and var. kafiristanica). No fruits were found on any of the individuals observed, and so discrimination between the varieties is impossible with this key. Nevertheless, cross-section of the stem revealed that the stem is hollow, a characteristic known to occur with the fiber-producing strains of *C. sativa* ssp. *sativa*, and thought to be absent from the intoxicating taxa in the genus. As such, these plants appear to be hybrids of the two subspecies of '*Cannabis sativa*', e.g., '*C. sativa* s.' and '*C. s. indica*'.

Origin, form, and growth characteristics:

*Origin*.—Whole Plant Natural Mutation of the F1 cultivar Pleadian.

*Propagation*.—The strain is perpetuated solely by cuttings.

*Mature habit*.—Tap-rooted annual, with extensive fibrous root system, upright and much branched aerial portion of plant. The growth form of all cloned individuals seen (n=10) was highly manipulated by systematic removal of terminal buds, inducing a greater branching habit. Overall size in this form varies in the population from 1.6-1.9 m tall and 0.3-0.4 m across at their widest point. Many petiole scars on stems from systematic removal of large shade leaves. In this habit, these are obviously very vigorous annual herbs.

*Growth*.—Very vigorous annuals herbs.

Foliage: Leaves.

*Arrangement*.—Alternate.

*Form*.—Palmately compound, (3) 5-7 (9) linear-lanceolate leaflets with glandular hairs.

*Size*.—Remaining (those still present when plants were observed) shade leaves, whole.

*Leaf* (*with petiole*).—18-20 cm long; middle (largest) leaflet 10-12 cm long, 2.8 cm wide.

*Margins*.—Coarsely serrate.

*Color*.—Top — dark green, Pantone PMS 364.

*Color*.—Bottom — light green, Pantone PMS 377.

*Veins, bottom*.—Pronounced midrib, with straight axial branches at about 45° angle, toward distal end of leaflet.

*Color*.—Light green, Pantone PMS 377.

*Petiole*.—Length: 9-10 cm at maturity.

*Color*.—Light green, Pantone PMS 377 as in the lower leaf surfaces.

*Stipules*.—Sometimes present at base of petiole, 0.5 cm long, bulbous bases, acuminate (tapering concave to apex).

*Aroma*.—Strongly mephitic, with hints of limonene, a cyclic terpene in Pinus ponderosa.

Stem: Hollow, large, rugose, punctuate, minutely glandular, ribbed, with ribs running parallel to stem, 2.0-2.5 cm diameter at base.

*Color*.—Bottom — light green, Pantone PMS 377. A few eglandular branched hairs.

*Height*.—1.5-1.9 m at anthesis following heavy pruning regime in cultivation.

Inflorescence:

*Blooming habit*.—Elongated compound cymes or panicles, forming spikes from 0.3-0.5 m in length, densely packed with individual small pistillate flowers subtended by small leaves, these with densely packed capitate glandular trichomes.

Flowers:

*Corolla*.—Petals and calyx unified and collectively appressed to and surrounding the ovary.

*Color*.—Light green, Pantone 372.

*Diameter*.—Individual pistillate flowers 2-3 mm, cyme 5-10 cm diameter.

*Shape*.—Urceolate (urn-shaped).

*Involucral bracts*.—Absent, but two highly glandular, urceolate bracteoles enclose the flower.

*Calyces*.—Appressed to the base of the ovary with the corolla as a unified perianth.

*Color*.—Green, Pantone PMS 364.

*Filaments*.—N/A — no staminate flowers observed.

*Stigma*.—Length 5-7 mm, ca. 1 mm wide at base, tapering to distal end. Densely covered with minute (<1 mm) soft, straight hairs.

*Color*.—Lemony white, Pantone PMS 372, drying slowly to red from apex to base after anthesis.

*Number*.—2.

*Staminate column*.—N/A — no staminate flowers observed.

*Fruit*.—An achene in this genus; however, no fruits were seen as all pistillate flowers were sterile.

*Pollen*.—N/A — no staminate flowers observed. Color: N/A — no staminate flowers observed.

*Petalage*.—The plant is essentially without petals (apetalous); these fused and appressed to the base of the ovary with the calyx as the perianth.

Flowers:

*Pedicel*.—flowers are essentially sessile (attached directly to the stem), and as such have no pedicel. The color chart referenced is standard hexadecimal Web Pantone Color Chart well known to those of ordinary skill in Internet web site design.

General characteristics and culture:

*Blooming period*.—Cuttings after rooting will bloom in 9-11 weeks when <12 hrs light applied to induce flowering.

*Hardiness*.—Probably fairly hardy; however, hardiness in nature unknown as this plant has only been cultivated in controlled conditions.

*Breaking action*.—Stems are fibrous, strong, and flexible; highly resistant to breakage.

*Rooting*.—>95% success rate with cuttings using CLONEX® a vitamin B1 rooting compound.

*Growth regulator*.—No growth regulators or other hormones used in cultivation.

*Shipping tolerance*.—Not applicable. This plant has never been shipped and is not intended for live shipment or household cultivation.

It is claimed:

1. A new and distinct cultivar of '*Cannabis*' plant, as shown and described.

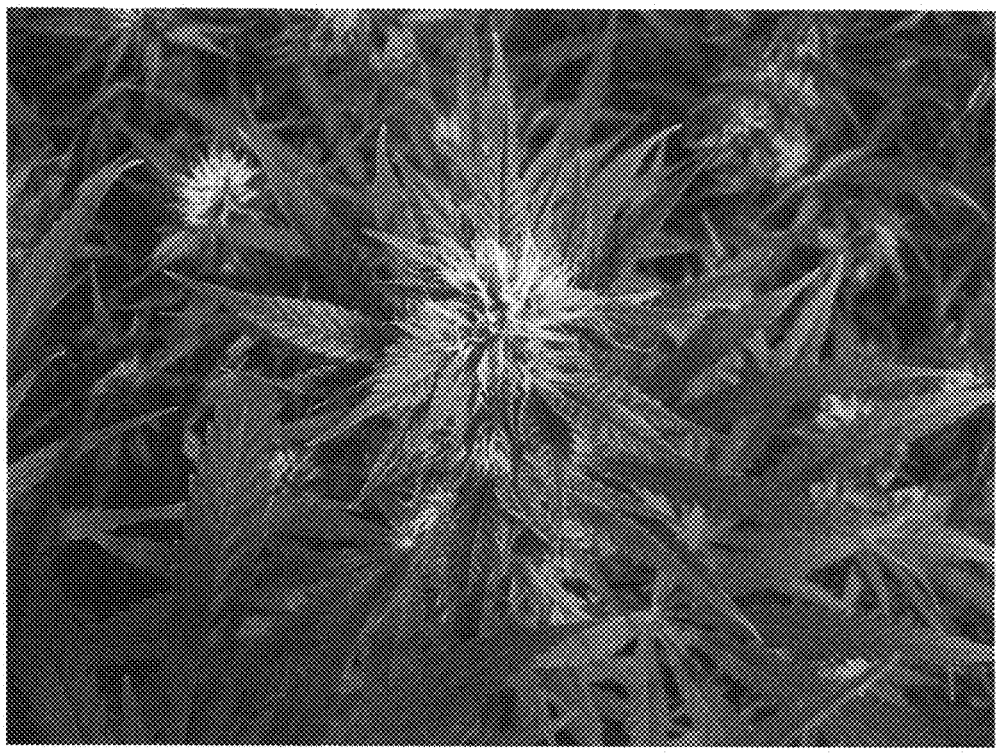

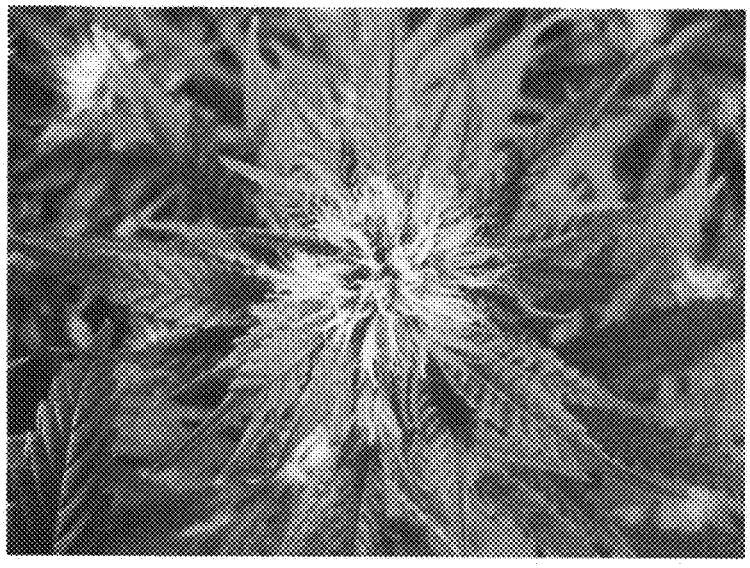

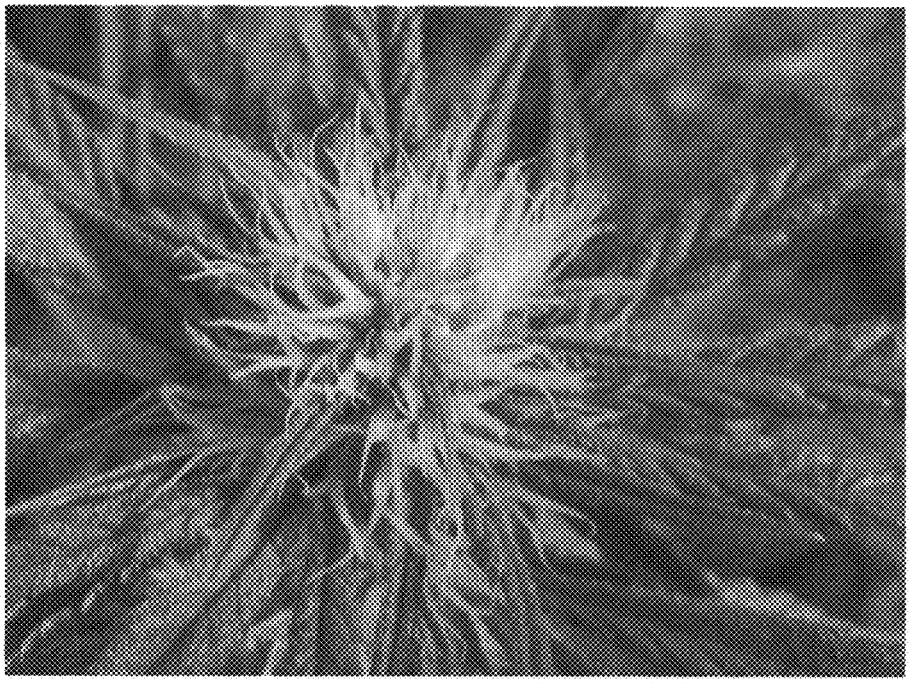

* * * * *